United States Patent
Kaidoh et al.

(10) Patent No.: US 7,446,128 B2
(45) Date of Patent: Nov. 4, 2008

(54) AGENT FOR TREATING INTERSTITIAL CYSTITIS

(75) Inventors: Kouichi Kaidoh, Azumino (JP); Satoshi Akahane, Azumino (JP)

(73) Assignee: Kissei Pharmaceutical Co., Ltd., Nagano (JP)

(*) Notice: Subject to any disclaimer, the term of this patent is extended or adjusted under 35 U.S.C. 154(b) by 0 days.

(21) Appl. No.: 11/267,299

(22) Filed: Nov. 7, 2005

(65) Prior Publication Data

US 2006/0100275 A1    May 11, 2006

(30) Foreign Application Priority Data

Nov. 10, 2004   (JP)   ............................. 2004-325992

(51) Int. Cl.
*A61N 31/24*   (2006.01)
*C07C 229/00*   (2006.01)

(52) U.S. Cl. .................... 514/538; 514/534; 560/37
(58) Field of Classification Search ............ 560/42, 560/37; 562/451; 514/532, 539, 540, 567, 514/568, 617, 538, 534

See application file for complete search history.

(56) References Cited

U.S. PATENT DOCUMENTS

| | | | |
|---|---|---|---|
| 6,538,152 B1 | 3/2003 | Tanaka et al. | |
| 2004/0138252 A1 | 7/2004 | Ikeda et al. | |
| 2004/0229947 A1 | 11/2004 | Yamazaki et al. | |

FOREIGN PATENT DOCUMENTS

EP   1 095 932 A1   5/2001

(Continued)

OTHER PUBLICATIONS

Shigeru Itabashi, et al.; Evidence that an atypical β-adrenoceptor mediates the prejunctional inhibition of non-adrengeric non-cholinergic contraction in guinea-pig bronchi; European Journal of Pharmacology, vol. 218, 1992, p. 187-190.

(Continued)

*Primary Examiner*—Taylor Victor Oh
(74) *Attorney, Agent, or Firm*—Sughrue Mion, PLLC

(57) ABSTRACT

A compound which can be used as an agent for treating interstitial cystitis. An agent for treating interstitial cystitis, which comprises a phenoxyacetic acid derivative represented by a general formula (I)

(I)

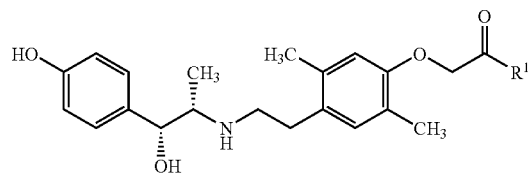

wherein $R^1$ represents hydroxyl group or a lower alkoxy group, or a pharmacologically acceptable salt thereof. Since the phenoxyacetic acid derivative represented by the general formula (I) or a pharmacologically acceptable salt thereof or a hydrate or solvate thereof has a selective $\beta_3$-adrenoceptor stimulating activity and a remarkable action to inhibit a capsaicin-sensitive sensory nerve, it can be used as a preventive or therapeutic agent for interstitial cystitis and hyperactive bladder which are accompanied by pain, other diseases in which the capsaicin-sensitive sensory nerve is concerned (e.g., acute or chronic and systemic or topical pain and inflammation) and irritable bowel syndrome (IBS) and the like.

4 Claims, 1 Drawing Sheet

FOREIGN PATENT DOCUMENTS

| EP | 1 405 638 A1 | 4/2004 |
|---|---|---|
| EP | 1 426 355 A1 | 6/2004 |
| WO | WO 00/02846 | 1/2000 |
| WO | WO 03/006019 A1 | 1/2003 |
| WO | WO 03/024916 A1 | 3/2003 |
| WO | WO 2004/098586 A1 | 11/2004 |

OTHER PUBLICATIONS

Diagnosis of interstitial cystitis; Urinary Disturbance Practice vol. 12, No. 1. 2004 p. 30-37.

Interstitial cystitis and C-fiber; Urinary Disturbance Practice vol. 12; No. 2004; p. 50-57.

The Merck Index; 1989; pp. 1355, 1359 and 1360.

Prematurity: Problems in Newborns: Merck Manual Home Edition, no date, pp. 1 to 3.

The Journal of Urology; Summary of the National Institute of Arthritis, Diabetes, Digestive and Kidney Diseases Workshop on Interstitial Cystitis, National Institutes of Health, Bethesda, Maryland, Aug. 28-29, 1987; pp. 203-206.

Hanno et al., "The Diagnosis of Interstitial Cystitis Revisited: Lessons Learned from the National Institutes of Health Interstitial Cystitis Database; Study" The Journal of Urology, Feb. 1999, vol. 161, pp. 553-557.

AGENT FOR TREATING INTERSTITIAL CYSTITIS

FIELD OF THE INVENTION

The present invention relates to an agent for treating interstitial cystitis. In particular, the present invention relates to an agent for treating interstitial cystitis, which comprises a phenoxyacetic acid derivative or a pharmacologically acceptable salt thereof or a hydrate or solvate thereof.

BACKGROUND OF THE INVENTION

Interstitial cystitis is an disorder of the bladder, which is accompanied by urinary urgency, pollakiuria and pain in the abdominal region and perineal region but is not accompanied by infections and particular pathologic findings. Interstitial cystitis causes very serious symptoms among the cystitis, which shows inflammation of the entire bladder wall extending not only to the mucous membrane but also to the muscle layer. Regarding the cause, breakdown of the bladder mucous membrane barrier function, elongation of a sensory nerve, C fiber, toward the mucous membrane side, concern of mast cell in the vicinity of C fiber, and the like have been suggested (cf., Non-patent Reference 1).

As the agent for treating interstitial cystitis, oral administration of a tricyclic antidepressant, an antihistaminic, a steroid, suplatast tosilate, pentosan polysulfate sodium, a Ca antagonist or the like, intravesical instillation therapy of heparin, hyaluronic acid, dimethyl sulfoxide (DMSO), capsaicin, resiniferatoxin or the like, and the like are generally used.

Among these, it is considered that the functional mechanism of capsaicin and resiniferatoxin is desensitization of C fiber, namely capsaicin-sensitive sensory nerve, and it has been reported that guinuclidin-3'-yl 1-phenyl-1,2,3,4-tetrahydroisoquinoline-2-carboxylate having a muscarine $M_3$ receptor-selective binding activity has a capsaicin-sensitive sensory nerve inhibitory action (cf., Patent Reference 1).

By the way, it has been reported that a phenoxyacetic acid derivative represented by a general formula (I) or a pharmacologically acceptable salt thereof or a hydrate or solvate thereof has a selective $\beta_3$-adrenoceptor stimulating activity and therefore is useful as a preventive or therapeutic agent for diseases caused by obesity, hyperglycemia or acceleration of movement of intestine and diseases caused by pollakiuria, urinary incontinence, depression, gallstone or acceleration of biliary movement (cf., Patent Reference 2). However, there are no report or suggestion on the relationship between phenoxyacetic acid derivatives and capsaicin-sensitive sensory nerve inhibiting activity.

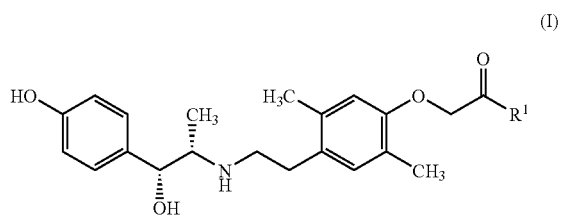

(I)

wherein $R^1$ represents hydroxyl group or a lower alkoxy group.

Non-patent Reference 1: Hainyo Shogai Practice (Urinary Disturbance Practice), published by Medical Review, 2004, Vol. 12, No. 1.

Patent Reference 1: International Publication WO 03/006019
Patent Reference 2: International Publication WO 00/02846

SUMMARY OF THE INVENTION

The present invention aims at providing an agent for treating interstitial cystitis.

Taking the aforementioned problems into consideration, the present inventors have conducted extensive studies and found that a phenoxyacetic acid derivative represented by the aforementioned general formula (I) has an activity to inhibit capsaicin-sensitive sensory nerve and therefore is remarkably effective for interstitial cystitis, thus accomplishing the present invention.

That is, the gist of the invention resides in an agent for treating interstitial cystitis, which comprises a phenoxyacetic acid derivative represented by a general formula (I) or a pharmacologically acceptable salt thereof or a hydrate or solvate thereof, and in a capsaicin-sensitive sensory nerve inhibitor.

Since the phenoxyacetic acid derivative represented by the general formula (I) or a pharmacologically acceptable salt thereof or a hydrate or solvate thereof has a selective $\beta_3$-adrenoceptor stimulating activity and a capsaicin-sensitive sensory nerve inhibiting activity, it can be used for the treatment of interstitial cystitis, particularly an interstitial cystitis which is accompanied by pain.

BRIEF DESCRIPTION OF THE DRAWINGS

By way of example and to make the description more clear, reference is made to the accompanying drawing in which.

DETAILED DESCRIPTION OF THE INVENTION

Figure 1:
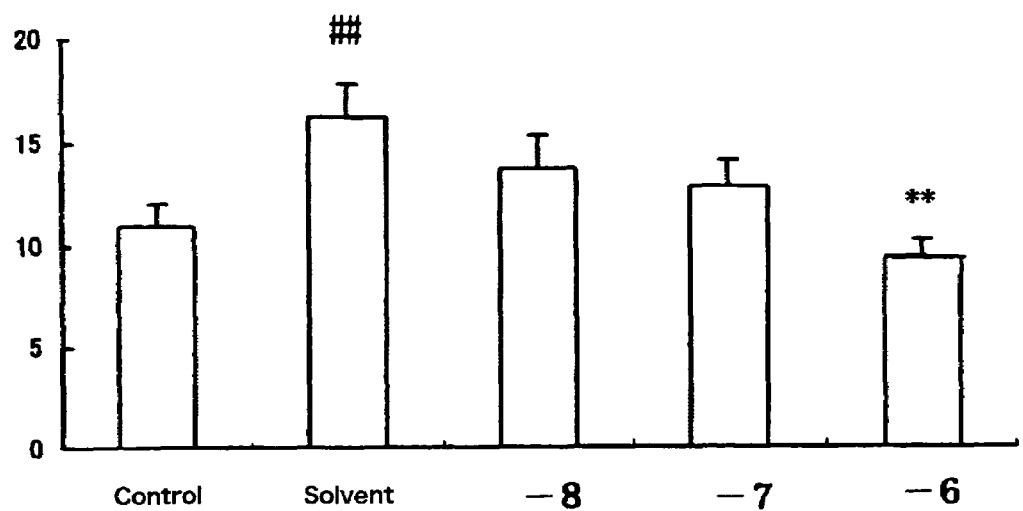
FIG. 1 is a graph showing the action of compound 1 to inhibit capsaicin-sensitive sensory nerve. The ordinate represents the amount of Evans Blue pigment (ng/mg·bladder wet weight), and the abscissa represents concentration of compound 1 (log[compound 1](mol/l)). The sign ## represents $p<0.05$ (control group), and ** $p<0.05$ (solvent group).
Figure 2:
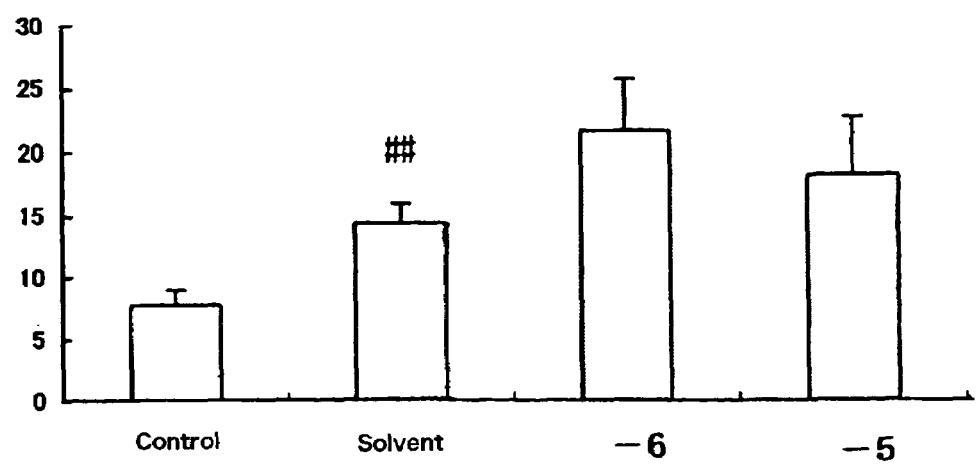
FIG. 2 is a graph showing the action of Tolterodine to inhibit capsaicin-sensitive sensory nerve. The ordinate represents the amount of Evans Blue pigment (ng/mg·bladder set weight), and the abscissa represents concentration of Tolterodine (log[Tolterodine](mol/l)). The sign ## represents $p<0.05$ (control group).

In the general formula (I), the lower alkoxy group means a straight chain or branched-chain alkoxy group having from 1 to 6 carbon atoms, preferably from 1 to 3 carbon atoms.

A phenoxyacetic acid derivative of general formula (I) can be produced by the method described in Patent Reference 2, and ethyl (−)-2-[4-[2-[[(1S,2R)-2-hydroxy-2-(4-hydroxyphenyl)-1-methylethyl]amino]ethyl]-2,5-dimethylphenoxy]acetate is desirable as the phenoxyacetic acid derivative.

As the pharmacologically acceptable salt of a phenoxyacetic acid derivative, for example, salts with sodium, potassium, calcium and the like inorganic bases; and salts with morpholine, piperidine and the like organic amines can be cited.

The agent for treating interstitial cystitis according to the invention can be produced by mixing a phenoxyacetic acid derivative represented by the general formula (I) or a pharmacologically acceptable salt thereof or a hydrate or solvate thereof with conventionally used pharmaceutical carriers.

The pharmaceutical carriers may be used by optionally combining them in response to each dosage form, and their examples include lactose and the like fillers; magnesium stearate and the like lubricants; carboxymethylcellulose and the like disintegrators; hydroxypropylmethylcellulose and the like binders; macrogol and the like surfactants; sodium bicarbonate and the like foaming agents; cyclodextrin and the like solubilizing agents; citric acid and the like sour taste agents; sodium edetate and the like stabilizers; phosphate and the like pH adjusting agents and the like.

Regarding the dosage form of the agent for treating interstitial cystitis according to the invention, for example, powders, granules, fine subtilaes, dry syrups, tablets, capsules and the like oral administration preparations; injections, adhesive preparations, suppositories and the like parenteral administration preparations, and the like can be cited, of which the oral administration preparations are desirable.

It is desirable to prepare the aforementioned pharmaceutical preparations in such a manner that a phenoxyacetic acid derivative represented by the general formula (I) or a pharmacologically acceptable salt thereof or a hydrate or solvate thereof can be administered within the range of from 1 to 1000 mg, particularly from 0.01 to 100 mg, per day per adult as oral administration preparations, once a day or dividing the daily dose into several doses.

The agent for treating interstitial cystitis according to the invention may further contain other drugs for interstitial cystitis, preferably a drug for interstitial cystitis having different functional mechanism. As the drug for interstitial cystitis having different functional mechanism, the aforementioned tricyclic antidepressant, antihistaminic, steroid, suplatast tosilate, pentosan polysulfate sodium, Ca antagonist, heparin, hyaluronic acid and the like can be exemplified.

EXAMPLES

The present invention is described further in detail in the following based on Examples, but the invention is not limited to the contents.

Test Example 1

A female Balb/c mouse (Japan SLC) which had been anesthetized by intraperitoneally administering 0.15 ml of 20% urethane was subjected to tracheal cannulation, using a polyethylene tube PE 50. A polyethylene tube PE 10 was inserted into the bladder via a urethra, and hydrochloride of ethyl (−)-2-[4-[2-[[(1S,2R)-2-hydroxy-2-(4-hydroxyphenyl)-1-methylethyl]amino]ethyl]-2,5-dimethylphenoxy]acetate (to be referred to as "compound 1" hereinafter), which had been dissolved in physiological saline and 2 equivalents of sodium hydroxide to a concentration of 10 μM and further diluted to various concentrations with physiological saline, was injected through the tube. After 1 hour from the injection, a solution (10 ml/kg) of Evans Blue (30 mg/kg) and capsaicin (0.3 mg/kg) dissolved in physiological saline containing 0.1% DMSO and 0.1% Tween 80 was administered through caudal vein. Precisely 5 minutes after the administration, the animal was sacrificed by cervical vertebrae dislocation to extract the bladder. After removing urine and blood from the extracted bladder, wet weight of the bladder was measured, and the extracted bladder was put into each well of a 96 well microplate into which formamide had been dispensed in 150 μl portions in advance. After soaking the bladder overnight in formamide, the pigment in the bladder tissue was determined by measuring absorbance of 100 μl of the supernatant at a wavelength of 620 nm. In addition, the amount of the Evans Blue pigment per 1 mg bladder wet weight was calculated. In this connection, a mouse in which physiological saline was injected into the bladder and the Evans Blue solution containing no capsaicin was administered thereto was used as the normal control.

The results are shown in FIG. 1 by average value±standard deviation. Inter-group significant difference between normal control group and capsaicin stimulation group was examined by student's t-test. Inter-group significant difference between compound 1 administration group and un-administration group was examined by a one dimensional analysis of variation and subsequent Dunnett's inter-multigroup comparison. A value of $p<0.05$ was regarded as significant.

Between the control group and solvent group, the amount of Evans Blue pigment was significantly high in the solvent group ($p<0.01$). In addition, the compound 1 concentration-dependently reduced the amount of Evans Blue pigment. Particularly, the amount of Evans Blue pigment was significantly reduced in the 1 μM administration group ($p<0.01$), which was the same level of the control group.

Test Example 2

The pigment in the bladder tissue was determined in the same manner as in Test Example 1, except that Tolterodine was used instead of the compound 1 and Hartman's solution was used instead of the physiological saline and 2 equivalents of sodium hydroxide. In this connection, a mouse in which Hartman's solution was injected into the bladder and the Evans Blue solution containing no capsaicin was administered thereto was used as the normal control.

Between the control group and solvent group, the amount of Evans Blue pigment was significantly high in the solvent group ($p<0.01$). Significant difference in the amount of Evans Blue pigment was not found between the Tolterodine administration group and solvent group.

The compound 1 which has a selective $\beta_3$-adrenoceptor stimulatory action markedly inhibited the capsaicin-sensitive sensory nerve, but the Tolterodine having a muscarine receptor antagonism did not inhibit the capsaicin-sensitive sensory nerve.

INDUSTRIAL APPLICABILITY

Since the phenoxyacetic acid derivative represented by the general formula (I) or a pharmacologically acceptable salt thereof or a hydrate or solvate thereof has a selective $\beta_3$-adrenoceptor stimulatory action and a remarkable action to inhibit the capsaicin-sensitive sensory nerve, it can be used as a preventive or therapeutic agent for interstitial cystitis and hyperactive bladder which accompany pain, other diseases in which the capsaicin-sensitive sensory nerve is concerned (e.g., acute or chronic and systemic or topical pain and inflammation) and irritable bowel syndrome (IBS) and the like.

While the invention has been described in detail and with reference to specific embodiments thereof, it will be apparent to one skilled in the art that various changes and modifications can be made therein without departing from the scope thereof.

This application is based on Japanese patent application No. 2004-325992 filed Nov. 10, 2004, the entire contents thereof being hereby incorporated by reference.

What is claimed is:

1. A method for treating pain caused by interstitial cystitis, which comprises administering a therapeutically effective amount of a phenoxyacetic acid derivative represented by the formula (I):

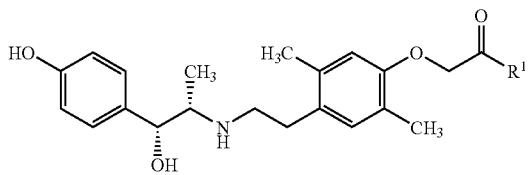

(I)

wherein R[1] represents hydroxyl group or a lower alkoxy group, or a pharmacologically acceptable salt thereof.

2. The method for treating pain caused by interstitial cystitis according to claim 1, wherein the phenoxyacetic acid derivative is ethyl (−)-2-[4-[2-[[(1S,2R)-2-hydroxy-2-(4-hydroxyphenyl)-1-methylethyl]amino]ethyl]-2,5-dimethylphenoxy] acetate.

3. The method of claim 1, wherein the compounds of formula (I) have selective $\beta_3$-adrenoceptor stimulating activity and will inhibit capsaicin-sensitive sensory nerves to thereby treat said pain caused by interstitial cystitis.

4. A method for treating pain caused by interstitial cystitis, which comprises administering a therapeutically effective amount of ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride.

* * * * *